United States Patent [19]

Trofimov et al.

[11] 4,077,975

[45] Mar. 7, 1978

[54] 1-VINYL-4,5,6,7-TETRAHYDROINDOLE AND PREPARATION THEREOF

[76] Inventors: Boris Alexandrovich Trofimov, ulitsa Lermontova, 321A, kv. 32; Alexandr Spiridonovich Atavin, ulitsa Lenina, 25, kv. 21; Albina Ivanovna Mikhaleva, ulitsa Lermontova, 291, kv. 6; Gennady Alexandrovich Kalabin, ulitsa Lenina, 25, kv. 18; Ekaterina Grigorievna Chebatareva, Teatralnaya ulitsa, 19, kv. 8, all of Irkutsk, U.S.S.R.

[21] Appl. No.: 625,320

[22] Filed: Oct. 23, 1975

[51] Int. Cl.$^2$ .......................................... C07D 209/04
[52] U.S. Cl. ............................ 260/319.1; 260/566 A; 424/274; 526/259
[58] Field of Search ....................................... 260/319.1

[56] References Cited

U.S. PATENT DOCUMENTS 3,652,585   3/1972   Remers et al. .................... 260/319.1

OTHER PUBLICATIONS

Dorie, Chemical Abstracts, vol. 53, 21868c (1959).

*Primary Examiner*—Dolph H. Torrence
*Attorney, Agent, or Firm*—Haseltine, Lake & Waters

[57] ABSTRACT

The present invention relates to a novel chemical compound, viz. 1-vinyl-4,5,6,7-tetrahydroindole of the formula:

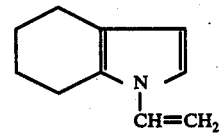

and to a method of preparing same.

In accordance with the invention, the method of preparing 1-vinyl-4,5,6,7-tetrahydroindole comprises reacting cyclohexanone oxime with acetylene at a molar ratio therebetween of 1:2-5 respectively at a temperature ranging from 70° to 170° C. Said reaction is effected in the presence of a basic catalyst in an amount of from 1 to 50% by weight of cyclohexanone oxime and in polar solvents or in a mixture of polar and non-polar solvents taken in a volumetric ratio to cyclohexanone oxime of 1-25:1-10 respectively. As a result of said reaction a reaction mixture is formed containing the desired product.

The desired product yield is ensured by the method of the present invention as high as 90-95%. The product requires no special purification treatment. The process is technologically simple.

8 Claims, No Drawings

1-VINYL-4,5,6,7-TETRAHYDROINDOLE AND PREPARATION THEREOF

The present invention relates to a novel chemical compound, viz. 1-vinyl-4,5,6,7-tetrahydroindole and to a method of preparing same.

Said compound, in accordance with the present invention, has the following formula:

1-vinyl-4,5,6,7-tetrahydroindole is a mobile colorless liquid with a weak indole odor which becomes yellow upon storage, readily forms colored complexes with salts of transition metals which complexes feature semiconductive and catalytic properties; it also serves as a dye imparting durable intensive purpureal color to fabrics and polymeric materials.

1-vinyl-4,5,6,7-tetrahydroindole is useful in radioelectronics and photography as a monomer for the preparation of photo-sensitive electroconductive films and layers, polymeric charge transfer complexes possessing catalytic and semiconductive properties. This compound may also be used in hydrometallurgy for the preparation of complex-forming extraction agents, sorbents and ion-exchange resins for recovering non-ferrous, rare and noble metals. Furthermore, this compound may be used as an insecticide selectively killing plant infestants, as well as intermediate products in the synthesis of dyes resembling natural ones and in the production of biologically active compounds.

In accordance with the present invention, a method of preparing 1-vinyl-4,5,6,7-tetrahydroindole comprises reacting cyclohexanone oxime with acetylene at a molar ratio therebetween of 1:2–5 respectively at a temperature within the range of from 70° to 170° C in the presence of a basic catalyst in an amount of from 1 to 50% by weight of cyclohexanone oxime and in a medium of polar solvents or a mixture of polar and non-polar solvents taken at a volumetric ratio, to cyclohexanone oxime, of 1–25:1–10 respectively with the formation of a reaction mixture containing the desired product.

Synthesis of 1-vinyl-4,5,6,7-tetrahydroindole is effected by means of a novel hitherto unknown reaction of acetylene which occurs in the presence of said catalyst and polar solvents in accordance with the following scheme:

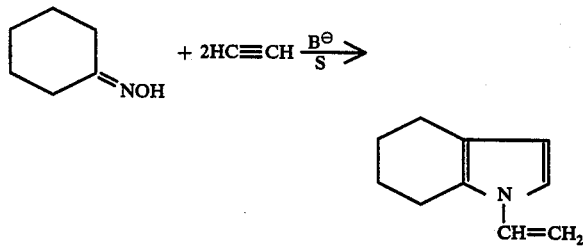

where B is a catalyst and S is a polar solvent.

Detailed description of the reaction is given hereinbelow

1. Proton extracting

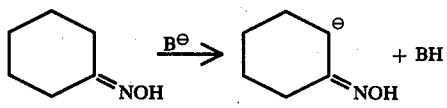

2. Addition of carbanion to acetylene

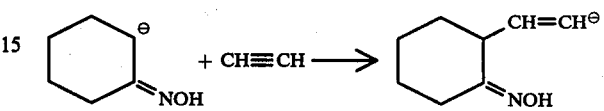

3. Intramolecular nucleophilic substitution at the nitrogen atom

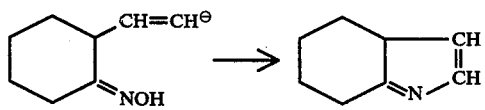

4. Rearrangement with the addition of another molecule of acetylene

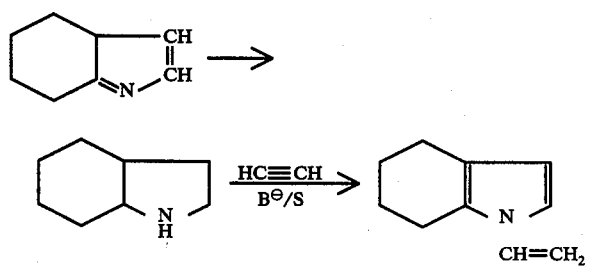

The structure of 1-vinyl-4,5,6,7-tetrahydroindole was proven by the spectrographic method of nuclear magnetic resonance (NMR) on nuclei $^1$H and $^{13}$C. The NMR spectrum of $^1$H involves two unresolved multiplets (4 protons each) with δ1.47 (protons in positions 5 and 6 of the indole skeleton) and 2.24 ppm (protons in positions 4 and 7) and 5 signals of different multiplicity within the range of 4.10 to 6.60 ppm (5 protons) relating to the fragment:

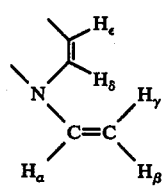

Proton designation, its chemical shift (±0.01 ppm), spin-spin interaction constant J(±0.1 Hz) are as follows: δ6.43; $J_{\alpha\beta}$8.9; $J_{\alpha\gamma}$15.6; $J_{\alpha\delta} \approx J_{\alpha\epsilon}$ 0.4; β4.21; $J_{\beta\gamma}$0.8; γ4.66; δ6.54; $J_{\delta\epsilon}$3.0; ε5.76.

NMR spectra of $^{13}$C were taken at a frequency of 25.2 MHz using the instrument XL-100/12 Varian; stabilization by deuterium (D$_2$O - external standard). Under conditions of proton noise decoupling the NMR spectrum of $^{13}C$ involves 10 signals, 6 of them being located within the range characteristic of aromatic and olefin nuclei of $^{13}C$. Given below are: (1) the number of $^{13}C$ nucleus according to the scheme:

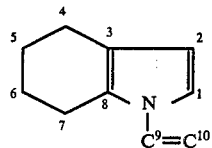

(2) the value of its chemical shift ($\pm 0.01$ ppm with respect to the $^{13}C$ signal of hexamethyldisiloxane, HMDS); (3) type of the signal without decoupling for $^{1}H$ and frequency value for irradiation within the range of NMR spectrum of $^{1}H$ (chemical shift of $\pm 0.1$ ppm is given with respect to the signal of HMDS ensuring the most favorable conditions for proton decoupling of said nucleus): 1, 112.46, doublet, 6.60; 2, 107.65, doublet, 5.75; 3, 116.86, singlet, 4.90; 4, 19.92, multiplet, 2.20; 5, 21.49, multiplet, 1.50; 6, 21.79 multiplet, 1.50; 7, 21.42 multiplet, 2.30; 8, 125.21, singlet, 5.00; 9, 128.41, doublet, 6.50; 10, 92.75, triplet, 4.45.

As the catalyst for the formation of 1-vinyl-4,5,6,7-tetrahydroindole use is made of such bases as oxides, hydroxides, and alcoholates of alkali and alkaline earth metals as well as said metals per se taken in an amount of from 1 to 50% by weight of cyclohexanone oxime. At a catalyst concentration below 1%, the reaction rate becomes too low, while at catalyst concentrations above 50% the reaction mixture becomes contaminated with the products of acetylene self-condensation.

The reaction should be conducted in the presence of polar solvents (sulfoxides, sulfons, amidophosphates, phosphine oxides) which are employed in a volumetric ratio, to cyclohexanone oxime, of 1-25:1-10 respectively.

The reaction may also be effected in the presence of either one polar solvent or a mixture of such solvents.

The use of more than 25-fold volumetric excess of the solvent is economically inefficient, while the use of an insufficient amount of the solvent (below the above-mentioned lower limit) necessitates elevated reaction temperatures resulting in the product resinification.

Under the above-described conditions, 1-vinyl-4,5,6,7-tetrahydroindole is formed at a temperature within the range of from 70° to 170° C. Below 70° C the reaction rate is very slow, while at a temperature above 170° C the rate of side reactions becomes sharply increased.

The preferred molar ratio between cyclohexanone oxime and acetylene is 1:3-4. At a lower ratio the resulting 1-vinyl-4,5,6,7-tetrahydroindole contains a contaminating compound, i.e. 4,5,6,7-tetrahydroindole which is difficult to separate.

Preferable proportions of the solvent and cyclohexanone oxime are within the range of 5-10:1.

It is advisable, to achieve high yields, that the reaction temperature be within the range of from 90° to 140° C in the presence of a catalyst in an amount of from 10 to 30% by weight of cyclohexanone oxime.

The process may be conducted under atmospheric and superatmospheric pressure in a closed, open or flow-type apparatus both continuously and periodically. It is advisable that operating pressures of acetylene be selected within the range of from 1 to 30 atm. In open and flow-type systems as well as in closed systems with small volumes of the solvent, the required ratio between acetylene and cylohexanone oxime is achieved progressively as acetylene is consumed.

In pure non-polar solvents the reaction does not occur, though it may proceed at an acceptable rate in mixtures of said solvents with polar solvents. In this case, it is advisable to use a non-polar solvent in a volumetric ratio to cyclohexanone oxime of 1-10:1 respectively. Non-polar solvents used in accordance with the present invention may be exemplified by hydrocarbons and cyclic ethers.

As the basic catalyst it is preferred to use potassium or sodium hydroxides, calcium oxide, potassium tert.butylate and tert.amylate as well as metallic sodium.

As the polar solvents use may be preferably made of dimethylsulfoxide, diethylsulfoxide, sulfolanes, hexamethyltriamidophosphate, triethylphosphine oxide, tert.butyl alcohol and tert.amyl alcohol, pyridine.

As the non-polar solvents use may be made of, for example, benzene and dioxane.

The process duration depends on the proportions and amounts of all the components of the reaction mixture, temperature and nature of the selected solvent. Thus at a temperature of from 120° to 140° C under acetylene pressure of from 5 to 15 atm in the presence of 5 to 30% of KOH by weight of cyclohexanone oxime in dimethylsulfoxide to complete the reaction it takes 1 to 3 hours.

Isolation of the desired product from the reaction mixture is performed by conventional methods: extraction or distillation or by a combination of both (depending on the solvent employed).

Under optimal conditions, conversion of cyclohexanone oxime to 1-vinyl-4,5,6,7-tetrahydroindole (calculated on the reacted oxime) may be as high as 70 to 90% and over.

The method according to the present invention has obvious commercial advantages: it is one-staged, simple in implementation, requires no special equipment or safety measures; it is performed in standard apparatus such as glass, ceramic or metallic vessels with a stirrer, bubbling columns or gas-lift type columns as well as in rotating autoclaves. Practically quantitative yield of the desired product ensures absence of wastes and waste waters. The starting materials (acetylene and cyclohexanone oxime) are commercially available and cheap (cyclohexanone oxime is an intermediate in the production of caprolactam); the solvents and catalyst employed are practically completely regenerated.

The method according to the present invention may be performed in one of the following embodiments thereof.

1. Cyclohexanone oxime, a catalyst and a solvent are charged into an autoclave and saturated with acetylene at room temperature under a pressure ranging from 1 to 20 atm. Thereafter, the autoclave is closed, heated to a temperature within the range of from 80° to 140° C and maintained at this temperature for a period of 1 to 3 hours. If the amount of acetylene is less than stoichiometrically required, the mixture is cooled and another portion of acetylene is fed; this operation is repeated till the cyclohexanone oxime-to-acetylene ratio of 1:3-4 is reached. The resulting reaction mixture is discharged and extracted with hydrocarbons such as benzene, toluene, hexane, gasoline or with ethers such as diethyl ether, vinyl-butyl ether or dibutyl ether; the extraction agent is then distilled off to give a crude product which is purified by distillation. If the solvent boiling point exceeds the product boiling point by more than 20° C, the product is isolated from the reaction mixture by distillation without any preliminary extraction. After separation of 1-vinyl-4,5,6,7-tetrahydroindole, the solvent containing the reaction catalyst is suitable for repeated use in the process without any additional purification and replenishment with a fresh portion thereof.

2. Into a vessel provided with a stirrer, cyclohexanone oxime, a catalyst and a solvent are charged; the vessel is connected to the source of acetylene supply and the reaction mixture is heated to the required temperature under stirring; acetylene pressure is maintained within the range of from 1 to 3 atm. Acetylene is admitted into the vessel continuously as it is consumed in the reaction, the pressure inside the apparatus being maintained constant. On completion of acetylene absorption, the reaction mixture is discharged and treated in a manner similar to that described in embodiment 1.

3. Same as embodiment 2, except that acetylene circulation is employed.

4. Acetylene is passed through a column containing the reaction mixture (cyclohexanone oxime, a catalyst and a solvent) under the required temperature and pressure conditions till its absorption is completed. The product is isolated as in embodiment 1.

Embodiments 1 to 4 may be performed as continuous processes with a constant discharge of the reaction mixture containing the desired product and with an adequate replenishment of cyclohexanone oxime, the solvent and catalyst.

For a better understanding of the present invention some specific examples are given hereinbelow.

EXAMPLE 1

5 g of cyclohexanone oxime, 1.5 g of potassium hydroxide and 120 ml of dimethylsulfoxide are placed into a one-liter rotary autoclave and saturated with acetylene under a pressure of 15 atm (40 l of acetylene are supplied in total). The autoclave is set on rotation and heated to the temperature of 120° C; this temperature is maintained for one hour, whereafter the heating is stopped. After cooling, the reaction mixture is discharged and thrice extracted with diethyl ether in portions of 50 ml each. The extract is washed with water, the ether is distilled-off and the resulting crude product is distilled to give 5.5 g (the yield is 93.2%) of 1-vinyl-4,5,6,7-tetrahydroindole boiling at 85°–86° C (3 mm Hg); $n_D^{20} = 1.5562$; $d_4^{20} = 1.0010$. Found, %: C 81.61, 81.61; H 8.67, 8.78; N 9.44, 9.28. $C_{10}H_{13}N$. Calculated, %: C 81,57; H 8.90; N 9.50.

EXAMPLE 2

5 g of cyclohexanone oxime, 0.5 g of potassium hydroxide and 40 ml of dimethylsulfoxide are placed into a one-liter rotary autoclave and saturated with acetylene under a pressure of 18 atm (25 l of acetylene are supplied in total). The autoclave is set on rotation and heated to the temperature of 140° C, maintained at this temperature for 1 hour and then is allowed to cool.

The resulting mixture is discharged, diluted with water (100 ml) and thrice extracted with benzene (portions of 30 ml each). Combined extracts are distilled to give 3.8 g (yield of 66%) of 1-vinyl-4,5,6,7-tetrahydroindole.

EXAMPLE 3

5 g of cyclohexanone oxime, 0.5 g of calcium oxide in 50 ml of hexamethyltriamidophosphate are heated with a 3-fold molar excess of acetylene (with reference to the stoichiometric amount thereof) to the temperature of 170° C in a one-liter rotary autoclave (maximal pressure is 30 atm). The cooled mixture is extracted with vinyl butyl ether and the extract is distilled to give 1.8 g (yield of 30%) of 1-vinyl-4,5,6,7-tetrahydroindole.

EXAMPLE 4

5 g of cyclohexanone oxime, 0.05 g of potassium tert.butylate and 0.5 g of triethylphosphine oxide are placed into a one-liter rotary autoclave which is filled with acetylene under the pressure of 12 atm and heated at the temperature of 70° C for 3 hours. After cooling, the autoclave is again filled with acetylene under the same pressure and again heated at 70° C for 3 hours. The resulting cooled mixture is extracted with dibutyl ether and the extract is distilled to give 1.4 g (yield of 24%) of 1-vinyl-4,5,6,7-tetrahydroindole.

EXAMPLE 5

0.5 g of metallic sodium is carefully dissolved in a mixture of 5 g of cyclohexanone oxime and 5 g of diethylsulfoxide. The resulting solution is heated with a 3-fold molar excess of acetylene (with respect to the stoichiometric amount thereof) in a one-liter rotary autoclave at a temperature of 100° C for a period of 2 hours. The reaction mixture is distilled to give 1.5 g (yield of 25%) of 1-vinyl-4,5,6,7-tetrahydroindole.

EXAMPLE 6

250 g of cyclohexanone oxime, 125 g of potassium hydroxide and 2.5 l of dimethylsulfoxide are placed into a 5 l reactor with a stirrer (1,500 r.p.m.) and, under continuous stirring acetylene is supplied for 6 hours under a pressure of 3 atm till its absorption by the reaction mass is completely stopped. After cooling, 500 ml of gasoline are charged into the reactor, the stirrer is switched on for 15 minutes. Thereafter, the mixture is allowed to settle and the resulting hydrocarbon layer is decanted by means of a siphon. The extraction is repeated 5 times. Distillation of the combined extracts results in 210 g of 1-vinyl-4,5,6,7-tetrahydroindole (yield is 71%).

The mixture of dimethylsulfoxide with the alkali remaining in the reactor is treated with another portion of 250 g of cyclohexanone oxime and the experiment is repeated to give 250 g (yield is 84.7%) of 1-vinyl-4,5,6,7-tetrahydroindole.

EXAMPLE 7

Into a glass column (height 1 m, volume 1.1 l) provided with an electric heater 100 g of cyclohexanone oxime, 40 g of KOH and 600 ml of dimethylsulfoxide are charged. Acetylene is passed through the column at a temperature of 150° C under atmospheric pressure until it is completely absorbed by the reaction mixture (10 hours). Extraction with benzene followed by distillation results in 78 g of 1-vinyl-4,5,6,7-tetrahydroindole (yield of 66%).

EXAMPLE 8

5 g of cyclohexanone oxime, 0.5 g of KOH, 50 ml of sulfolane and 50 ml of benzene are heated for 2 hours at a temperature of 110° C in a one-liter rotary autoclave in the presence of a 3-fold excess of acetylene (with respect to the stoichiometric amount thereof); maximal pressure being 23 atm.

The reaction mixture is extracted with benzene, washed with water and distilled to give 4.6 g (70%) of 1-vinyl-4,5,6,7-tetrahydroindole.

EXAMPLE 9

5 g of cyclohexanone oxime, 1 g of potassium tert.amylate, 125 ml of dimethylsulfoxide and 125 ml of tert-amyl alcohol are heated for a period of 3 hours at a temperature of 120° C in a one-liter rotary autoclave in the presence of a 4-fold excess of acetylene (with respect to the stoichiometric amount thereof). Maximal pressure is 29 atm. The reaction mixture is extracted with diethyl ether and distilled to give 5.6 g (94.9%) of 1-vinyl-4,5,6,7-tetrahydroindole.

EXAMPLE 10

5 g of cyclohexanone oxime, 2.5 g of sodium hydroxide, 100 ml of dimethylsulfoxide and 5 ml of pyridine are heated for 3 hours at a temperature of 90° C in a one-liter rotary autoclave in the presence of a 5-fold excess of acetylene (with respect to the stoichiometric amount thereof). Maximal pressure is 27 atm. The reaction mixture is extracted with diethyl ether and distilled to give 5.3 g (90%) of 1-vinyl-4,5,6,7-tetrahydroindole.

EXAMPLE 11

5 g of cyclohexanone oxime, 1 g of potassium hydroxide, 50 ml of dimethylsulfoxide and 50 ml of dioxane are heated for a period of one hour at the temperature of 140° C in the presence of a 5-fold excess of acetylene (with respect to the stoichiometric amount thereof). After extraction with diethyl ether and distillation 5.4 g (yield is 91.6%) of 1-vinyl-4,5,6,7-tetrahydroindole are obtained.

What is claimed is:

1. 1-vinyl-4,5,6,7-tetrahydroindole.

2. A method of preparing 1-vinyl-4,5,6,7-tetrahydroindole comprising reacting cyclohexanone oxime with acetylene at a molar ratio therebetween of 1:2–5 at a temperature within the range of from 70° to 170° C in the presence of a catalyst selected from the group consisting of alkali and alkaline earth metals and their oxides, hydroxides and alcoholates in an amount of from 1 to 50% by weight of cyclohexanone oxime and in a polar solvent selected from the group consisting of sulfoxides, sulfones, amidophosphates, phosphine oxides, t-butyl alcohol, t-amyl alcohol, pyridine, and mixtures thereof with a non-polar solvent selected from the group consisting of hydrocarbons and cyclic ethers, said solvent being taken in a volumetric ratio to cyclohexanone oxime of 1–25:1–10 with the formation of a reaction mixture containing the desired product.

3. A method as claimed in claim 2, wherein said reaction of cyclohexanone oxime with acetylene is effected at a molar ratio therebetween of 1:3–4 at a temperature of from 90° to 140° C with the catalyst taken in an amount of from 10 to 30% by weight of cyclohexanone oxime and a polar solvent selected from the group consisting of sulfoxides, sulfones, amidophosphates, phosphine oxides, t-butyl alcohol, t-amyl alcohol and pyridine taken in a volumetric ratio to cyclohexanone oxime of 5–10:1.

4. A method as claimed in claim 2, wherein said reaction of cyclohexanone oxime with acetylene is effected under a pressure of from 1 to 30 atm.

5. A method as claimed in claim 2, wherein said non-polar solvent is used in a volumetric ratio to cyclohexanone oxime of 1–10:1.

6. A method as claimed in claim 2, wherein the catalyst is selected from the group consisting of potassium hydroxide, sodium hydroxide, calcium oxide, potassium tert-butylate, potassium tert-amylate and metallic sodium.

7. A method as claimed in claim 2, wherein the polar solvent is selected from the group consisting of dimethylsulfoxide, diethylsulfolane, hexamethyltriamidophosphate and triethylphosphine oxide.

8. A method as claimed in claim 2, wherein the non-polar solvent is selected from the group consisting of benzene and dioxane.

* * * * *